United States Patent
Iguchi et al.

(10) Patent No.: US 9,611,236 B2
(45) Date of Patent: Apr. 4, 2017

(54) METHOD FOR PRODUCING ETHYLENE OXIDE

(71) Applicant: NIPPON SHOKUBAI CO., LTD., Osaka (JP)

(72) Inventors: Shingo Iguchi, Kanagawa (JP); Yukimasa Kawaguchi, Kanagawa (JP)

(73) Assignee: NIPPON SHOKUBAI CO., LTD., Osaka (JP)

(*) Notice: Subject to any disclaimer, the term of this patent is extended or adjusted under 35 U.S.C. 154(b) by 0 days.

(21) Appl. No.: 14/781,155

(22) PCT Filed: Mar. 28, 2014

(86) PCT No.: PCT/JP2014/059345
§ 371 (c)(1),
(2) Date: Sep. 29, 2015

(87) PCT Pub. No.: WO2014/157698
PCT Pub. Date: Oct. 2, 2014

(65) Prior Publication Data
US 2016/0052899 A1  Feb. 25, 2016

(30) Foreign Application Priority Data
Mar. 29, 2013 (JP) ................................. 2013-074174

(51) Int. Cl.
*C07D 301/10* (2006.01)

(52) U.S. Cl.
CPC .................. *C07D 301/10* (2013.01)

(58) Field of Classification Search
CPC .................................................. C07D 301/10
See application file for complete search history.

(56) References Cited

U.S. PATENT DOCUMENTS

| | | | |
|---|---|---|---|
| 3,964,980 A | 6/1976 | Ozero | |
| 4,778,567 A | 10/1988 | Kakimoto et al. | |
| 5,559,255 A | 9/1996 | Kawabe et al. | |
| 6,397,599 B1* | 6/2002 | Theis | C07C 29/106 60/649 |
| 8,580,982 B2* | 11/2013 | Seeber | C07D 301/10 549/536 |
| 9,096,562 B2* | 8/2015 | Rokicki | C07D 301/10 |

FOREIGN PATENT DOCUMENTS

| | | |
|---|---|---|
| JP | 60-131817 | 7/1985 |
| JP | 63-170206 | 7/1988 |
| JP | S63-170206 A | 7/1988 |
| JP | 2012-167072 | 9/2012 |

OTHER PUBLICATIONS

International Preliminary Report on Patentability dated Oct. 8, 2015 issued in PCT/JP2014/059345, an International Patent Application that corresponds to the present application.

* cited by examiner

*Primary Examiner* — Golam M M Shameem
(74) *Attorney, Agent, or Firm* — Porzio Bromberg & Newman, P.C.

(57) ABSTRACT

[Problem] To provide a method by which an amount of production of ethylene glycol as a by-product is reduced and a yield of ethylene oxide can be improved in a process for producing ethylene oxide.
[Solution] An embodiment of the present invention relates to a method for producing ethylene oxide. The method for producing ethylene oxide includes: supplying an ethylene oxide-containing reaction product gas produced in an ethylene oxidation reaction step, in which ethylene is subjected to catalytic gas-phase oxidation using a molecular oxygen-containing gas in the presence of a silver catalyst, to an ethylene oxide absorption column; bringing the reaction product gas into contact with an absorption liquid supplied to the ethylene oxide absorption column; supplying an ethylene oxide-containing column bottom liquid of the ethylene oxide absorption column to an ethylene oxide purification system; and supplying an ethylene oxide-containing uncondensed gas discharged from the ethylene oxide purification system to an ethylene oxide reabsorption column. In the method, an operation pressure of the ethylene oxide reabsorption column is set to 3 to 50 kPa gauge.

5 Claims, 3 Drawing Sheets

METHOD FOR PRODUCING ETHYLENE OXIDE

TECHNICAL FIELD

The present invention relates to a method for producing ethylene oxide.

BACKGROUND ART

Nowadays, ethylene oxide is produced by catalytic gas phase oxidation of ethylene using a molecular oxygen-containing gas in the presence of a silver catalyst. An outline of a purifying method in a process for producing ethylene oxide is as follows (for example, refer to JP 62-103072 A).

First, ethylene and a molecular oxygen-containing gas are subjected to catalytic gas phase oxidation on a silver catalyst to obtain an ethylene oxide-containing reaction product gas (reaction step). Subsequently, the resulting reaction product gas is introduced into an ethylene oxide absorption column. The reaction product gas is brought into contact with an absorption liquid mainly containing water. Ethylene oxide is recovered as an aqueous solution (absorption step). Subsequently, the recovered ethylene oxide aqueous solution is fed to a purification system of ethylene oxide to obtain high-purity ethylene oxide through several stages. The ethylene oxide purification system usually includes a stripping step, a purification step, a dehydration step, a light fraction separation step, a heavy fraction separation step, and the like.

Usually, an exhaust gas containing unreacted ethylene discharged from a column top part of the ethylene oxide absorption column, a carbon dioxide gas (carbon dioxide; $CO_2$) and water as by-products, and an inert gas (nitrogen, argon, methane, ethane, or the like) is circulated into an ethylene oxidation step as it is. Alternatively, apart thereof is extracted and introduced into a carbon dioxide gas absorption column, and the carbon dioxide gas is selectively absorbed by an alkali absorption liquid. The absorption liquid is supplied to a carbon dioxide gas stripper column to strip and recover the carbon dioxide gas (for example, refer to JP 60-131817 A).

SUMMARY OF INVENTION

Technical Problem

Here, an uncondensed gas discharged from the ethylene oxide purification system contains ethylene oxide. Therefore, the uncondensed gas is supplied to an ethylene oxide reabsorption column, and ethylene oxide is thereby reabsorbed. The resulting absorption liquid is circulated into the ethylene oxide purification system again to recover ethylene oxide.

However, when ethylene oxide is recovered in the ethylene oxide reabsorption column, a water molecule is attached to a part of ethylene oxide to cause a reaction to produce ethylene glycol in a process for feeding a column bottom liquid of the ethylene oxide absorption column after ethylene oxide is absorbed to an ethylene oxide stripper column or in the ethylene oxide stripper column. Such production of ethylene glycol as a by-product obstructs producing higher-purity ethylene oxide at a higher yield. Therefore, development of a method for suppressing such production of ethylene glycol as a by-product is desired. In order to prevent concentration of ethylene glycol in a system of a process for producing ethylene oxide, such a countermeasure as discharging a part of ethylene glycol to the outside of the system or feeding the part of ethylene glycol to an ethylene glycol production plant is made. However, these countermeasures disadvantageously lower a yield of ethylene oxide.

An object of the present invention is to provide a method by which an amount of production of ethylene glycol as a by-product is reduced and the yield of ethylene oxide can be improved in the process for producing ethylene oxide.

Means for Solving Problem

The present inventors made intensive studies to solve the above-described problems. As a result, the inventors have found that the above-described problems can be solved by making an operation pressure of the ethylene oxide reabsorption column lower than that in the related art, and have completed the present invention.

That is, an embodiment of the present invention relates to a method for producing ethylene oxide. The production method includes: supplying an ethylene oxide-containing reaction product gas produced in an ethylene oxidation reaction step, in which ethylene is subjected to catalytic gas phase oxidation using a molecular oxygen-containing gas in the presence of a silver catalyst, to an ethylene oxide absorption column; bringing the reaction product gas into contact with an absorption liquid supplied to the ethylene oxide absorption column; supplying an ethylene oxide-containing column bottom liquid of the ethylene oxide absorption column to an ethylene oxide purification system; and supplying an ethylene oxide-containing uncondensed gas discharged from the ethylene oxide purification system to an ethylene oxide reabsorption column. The production method is characterized in that the operation pressure of the ethylene oxide reabsorption column is 3 to 50 kPa gauge.

Advantageous Effect of the Invention

According to the present invention, an amount of production of ethylene glycol as a by-product is reduced and a yield of ethylene oxide is improved in a process for producing ethylene oxide. In addition, as a secondary effect, such an industrially extremely advantageous effect as follows is exhibited. That is, an amount of steam required for concentration of ethylene glycol as a by-product to be discharged to the outside of a system of the process for producing ethylene oxide, or an input amount of water necessary when the ethylene glycol as a by-product is discharged to the outside, is reduced.

BRIEF DESCRIPTION OF DRAWINGS

FIG. 2 corresponds to a stripping step employed in Example hereinafter described.

DESCRIPTION OF EMBODIMENTS

Hereinafter, specific embodiments for carrying out the present invention will be described in detail with reference to the drawings. However, the technical range of the present invention should be determined based on the description of claims, and is not limited only to the following embodiment.

<<Reaction System>>

Figure 1:
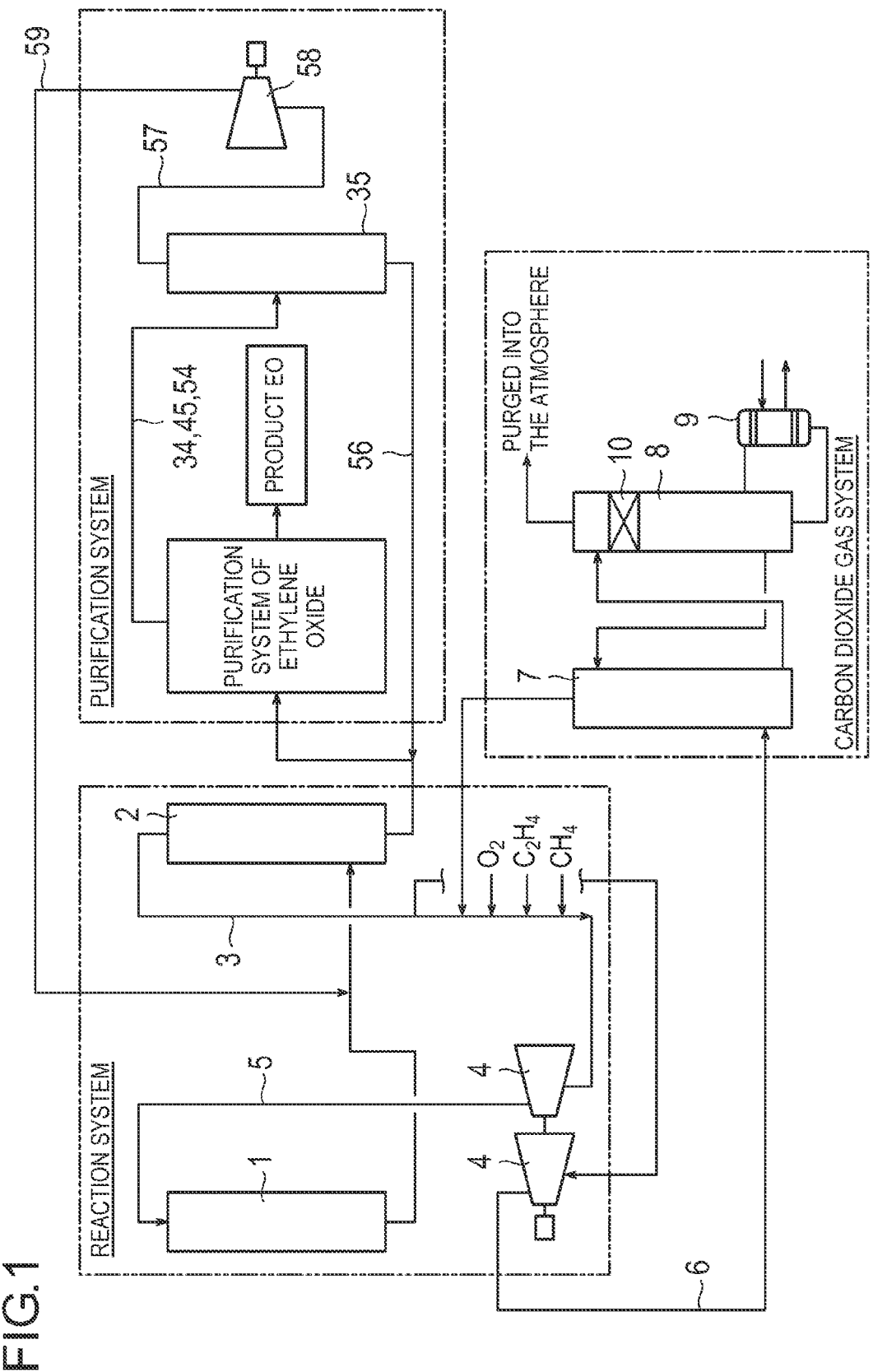
FIG. 1 is a block diagram illustrating a constructive example of a process for producing ethylene oxide, performing a method for producing ethylene oxide according to an embodiment of the present invention.

First, a system of producing ethylene oxide by an oxidation reaction of ethylene (hereinafter, also simply referred to as "reaction system") will be described with reference to FIG. 1. FIG. 1 is a block diagram illustrating a constructive example of a process for producing ethylene oxide, performing a method for producing ethylene oxide according to an embodiment of the present invention. The process for producing ethylene oxide illustrated in FIG. 1 is roughly divided into three systems of a reaction system, a carbon dioxide gas system, and a purification system.

"An ethylene oxide-containing reaction product gas" used in the present invention is only required to be produced by a step in which ethylene is subjected to catalytic gas phase oxidation using a molecular oxygen-containing gas in the presence of a silver catalyst (hereinafter, also referred to as "ethylene oxidation reaction step"). The technology itself of the catalytic gas phase oxidation reaction is popular, and conventionally known knowledge thereof can be appropriately referred to in order to carry out the present invention. Specific embodiments such as a composition of the reaction product gas are not particularly limited. As an example, the reaction product gas usually contains, in addition to ethylene oxide in an amount of 0.5 to 5% by volume, unreacted oxygen, unreacted ethylene, generated water, a gas such as carbon dioxide, nitrogen, argon, methane, or ethane, an aldehyde such as formaldehyde or acetaldehyde, and a small amount of an organic acid such as acetic acid.

When FIG. 1 is referred to, first, a raw material gas containing ethylene or molecular oxygen is boosted by a boosting blower 4, and then is heated by a heat exchanger (not illustrated) to be supplied to an ethylene oxidation reactor 1. The ethylene oxidation reactor 1 is usually a multi-tubular reactor provided with many reaction tubes filled with a silver catalyst. The reaction product gas produced in the ethylene oxidation reaction step is cooled by passing through a heat exchanger (not illustrated). Thereafter, the reaction product gas is supplied to an ethylene oxide absorption column (hereinafter, also simply referred to as "absorption column") 2. Specifically, the reaction product gas is supplied from a column bottom part of the absorption column 2. Meanwhile, an absorption liquid mainly containing water is supplied from a column top part of the absorption column 2. Counter flow contact between a gas and a liquid is thereby conducted in the absorption column 2. Ethylene oxide (usually, 99% by weight or more) included in the reaction product gas is absorbed in the absorption liquid. In addition to ethylene oxide, ethylene, oxygen, carbon dioxide, an inert gas (nitrogen, argon, methane, ethane, or the like), a low boiling point impurity such as formaldehyde, and a high boiling point impurity such as acetaldehyde or acetic acid, which are produced in the ethylene oxidation reaction step, are absorbed at the same time in substantial amounts thereof. The temperature of the reaction product gas supplied to the absorption column 2 is preferably about 20 to 80° C. A composition of the absorption liquid is not particularly limited. In addition to a liquid mainly containing water, such propylene carbonate as disclosed in JP 8-127573 A may be used as an absorption liquid. An additive can be added to the absorption liquid as necessary. Examples of the additive which can be added to the absorption liquid include a defoaming agent and a pH adjusting agent. As the defoaming agent, any defoaming agent which is insert to ethylene oxide, ethylene glycol as a by-product, or the like, and has a defoaming effect of the absorption liquid can be used. However, a typical example thereof is a water-soluble silicone emulsion because the water-soluble silicone emulsion is effective due to excellent dispersibility in the absorption liquid, excellent dilution stability, and excellent thermal stability. Examples of the pH adjusting agent include a compound which can be dissolved in the absorption liquid, such as a hydroxide or a carbonate of an alkali metal such as potassium or sodium. Preferable examples thereof include potassium hydroxide and sodium hydroxide. The pH of the absorption liquid is preferably 5 to 12, more preferably 6 to 11.

As the absorption column 2, a plate column type or packed column type absorption column can be usually used. As an operation condition of the absorption column 2, a concentration of ethylene oxide in the reaction product gas is 0.5 to 5% by volume, preferably 1.0 to 4% by volume, and an operation pressure of the absorption column 2 is 0.2 to 4.0 MPa gauge, preferably 1.0 to 3.0 MPa gauge. An absorption operation is more advantageous as the pressure is higher. However, a possible value thereof can be determined according to an operation pressure of the oxidation reactor. A molar ratio of flow rate (L/V) of the absorption liquid with respect to the reaction product gas is usually 0.30 to 2.00. A space linear velocity (GHSV[NTP]) of the reaction product gas under the standard state is usually 400 to 6000 $h^{-1}$.

A gas not absorbed in the absorption column 2, containing ethylene, oxygen, carbon dioxide, an inert gas (nitrogen, argon, methane, or ethane), aldehyde, an acid substance, or the like, is discharged from the column top part of the absorption column 2 through a conduit 3. The exhaust gas is boosted by the boosting blower 4, and then is circulated into the ethylene oxidation reactor 1 through a conduit 5. Details of the ethylene oxidation reaction step are as described above. Here, the ethylene oxidation reaction step is usually carried out in an oxidation reactor provided with many reaction tubes filled with a silver catalyst under pressure (pressure of about 1.0 to 3.0 MPa gauge). Therefore, it is necessary to boost the exhaust gas from the column top part of the absorption column 2 using a boosting unit such as the boosting blower 4 before the exhaust gas is circulated into the ethylene oxidation reaction step.

<<Carbon Dioxide Gas System>>

In a preferable embodiment, as illustrated in FIG. 1, at least a part of the gas discharged from the column top part of the absorption column 2 is boosted by a boosting unit such as the boosting blower 4 to be supplied to a carbon dioxide gas absorption column 7 through a conduit 6. Hereinafter, a carbon dioxide gas recovery system (hereinafter, also simply referred to as "carbon dioxide gas system") starting from introduction of a gas into the carbon dioxide gas absorption column 7 will be described with reference to FIG. 1.

As described above, when the gas discharged from the column top part of the absorption column 2 is boosted and introduced into the carbon dioxide gas absorption column 7, the gas pressure at that time is adjusted to about 0.2 to 4.0 MPa gauge, and the gas temperature is adjusted to about 80 to 120° C. A carbon dioxide gas stripper column 8 is disposed in a post-stage of the carbon dioxide gas absorption column 7. An alkali absorption liquid is supplied from a column bottom part of the carbon dioxide gas stripper column 8 to an upper part of the carbon dioxide gas absorption column 7. A carbon dioxide gas and a small amount of inert gas (for example, ethylene, methane, ethane, oxygen, nitrogen, argon), contained in the gas introduced into the carbon dioxide gas absorption column 7, are absorbed by counter flow contact with the alkali absorption liquid. An unabsorbed gas discharged from the column top part of the carbon dioxide gas absorption column 7 is circulated into the conduit 3, is mixed with oxygen, ethylene, methane, or the like newly replenished, and then is circulated into the ethylene oxidation reactor 1.

The carbon dioxide gas-rich absorption liquid which has absorbed the carbon dioxide gas in the carbon dioxide gas absorption column 7 is extracted from the column bottom part of the carbon dioxide gas absorption column. Thereafter, the pressure thereof is adjusted to 0.01 to 0.5 MPa gauge, and the temperature thereof is adjusted to about 80 to 120° C. The carbon dioxide gas-rich absorption liquid is supplied to an upper part of the carbon dioxide gas stripper column 8 provided with a reboiler 9 at the column bottom part thereof. The absorption liquid causes pressure flash due to a pressure difference between the carbon dioxide gas absorption column 7 and the carbon dioxide gas stripper column 8 in a liquid feeding part in the upper part of the carbon dioxide gas stripper column 8. Because of the pressure flash, 10 to 30% by volume of carbon dioxide gas and most inert gases in the absorption liquid are separated from the absorption liquid, and discharged from the column top part of the carbon dioxide gas stripper column 8.

The remaining carbon dioxide gas absorption liquid after a part of the carbon dioxide gas is separated because of the above-described pressure flash enters a gas-liquid contact part 10 provided below the liquid feeding part. The carbon dioxide gas absorption liquid is subjected to counter flow contact with a gas mainly containing steam produced in the reboiler 9 and a carbon dioxide gas produced in the gas-liquid contact part 10 or in parts below the gas-liquid contact part 10. Apart of the carbon dioxide gas in the absorption liquid and most of the other inert gases are separated from the absorption liquid. By a series of the processes in the carbon dioxide gas system, a high-purity carbon dioxide gas is obtained from a part ranging from the top to the lower part of the gas-liquid contact part 10, preferably from the inside of the carbon dioxide gas stripper column 8 below the gas-liquid contact part corresponding to one or more number of theoretical stages, necessary for gas-liquid contact. That is, in the gas-liquid contact part 10, the inert gas in the carbon dioxide gas absorption liquid is subjected to counter flow gas-liquid contact by water vapor and a carbon dioxide gas containing an extremely small amount of inert gas which comes up from the lower part, and is stripped. This makes the concentration of the inert gas extremely low. Therefore, if the gas after being stripped is extracted, a high-purity carbon dioxide gas is obtained.

<<Purification System>>

Figure 2:
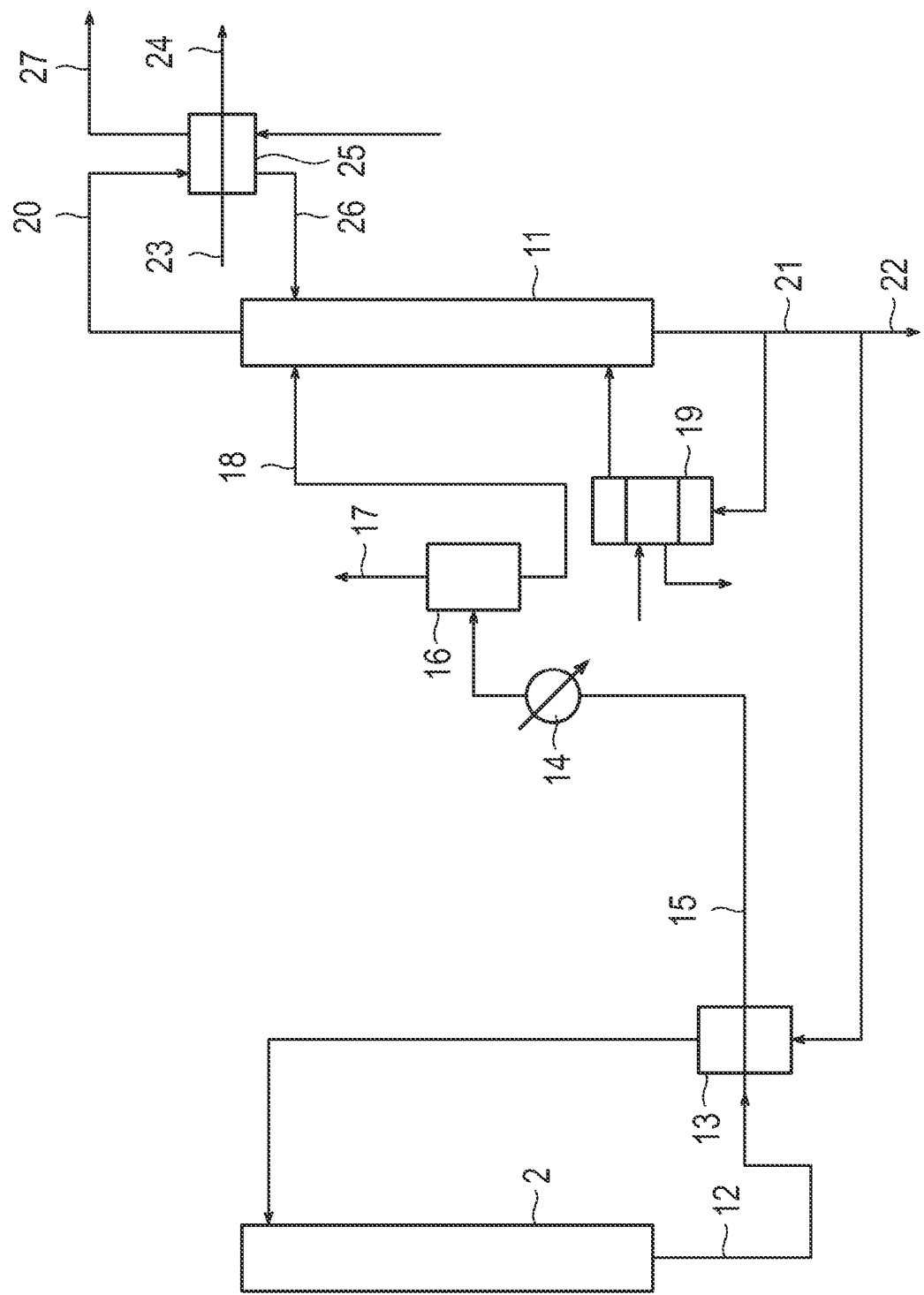
FIG. 2 is a block diagram illustrating a constructive example of a process for performing the process for producing ethylene oxide according to the embodiment of the present invention.

The absorption liquid which has absorbed ethylene oxide in the absorption column 2 is fed to an ethylene oxide purification system (hereinafter, also simply referred to as "purification system") as a column bottom liquid of the absorption column 2. Specific embodiments of the purification system are not particularly limited. Conventionally known knowledge thereof can be appropriately referred to. The purification system usually includes a stripping step, a purification step, a dehydration step, a light fraction separation step, a heavy fraction separation step, and the like. Hereinafter, a purification system including some of these steps will be described with reference to FIGS. 2 and 3. FIG. 2 is a block diagram illustrating a constructive example of a process for performing the process for producing ethylene oxide according to the embodiment of the present invention.

The column bottom liquid (absorption liquid) of the absorption column 2 is usually heated to a temperature suitable for stripping in an ethylene oxide stripper column (hereinafter, also simply referred to as "stripper column") 11 in advance before being supplied to the stripper column 11. Specifically, as illustrated in FIG. 2, the column bottom liquid (absorption liquid) of the absorption column 2 is supplied to a heat exchanger 13 through a conduit 12. In the heat exchanger 13, heat exchange with the column bottom liquid of the stripper column 11 is performed. Furthermore, if necessary, the column bottom liquid (absorption liquid) of the absorption column 2 is heated by a heater 14 to a temperature of about 70 to 110° C. In the present embodiment, the column bottom liquid (absorption liquid) of the absorption column 2, heated by heat exchange with the column bottom liquid of the stripper column 11, is supplied to a gas-liquid separation tank 16 through a conduit 15. In the gas-liquid separation tank 16, a light fraction gas of an inert gas partially including ethylene oxide and water is separated, and discharged through a conduit 17. On the other hand, the absorption liquid as a remaining part after the light fraction gas is flashed is supplied to an upper part of the stripper column 11 through a conduit 18. In a portion where ethylene oxide and water exist together at a particularly high temperature as in the conduit 18, staying time of the absorption liquid can be short by making a disposition distance thereof as short as possible. As a result, production of ethylene glycol as a by-product can be prevented.

Subsequently, for example, as illustrate in FIG. 2, a heating medium such as water vapor is supplied to a heater 19, and the stripper column 11 is heated using the heating medium heated in the heater 19. Alternatively, the stripper column 11 is heated by directly supplying water vapor to the column bottom part of the stripper column 11. By heating the stripper column 11 in such a manner, ethylene oxide contained in the absorption liquid supplied from the upper part of the stripper column 11 (usually 99% by weight or more thereof) is stripped and discharged from the column top part of the stripper column 11 through a conduit 20. As for operation conditions of the stripper column 11, an operation pressure (column top pressure) is 3 to 60 kPa gauge, preferably 3 to 30 kPa gauge. The smaller the column top pressure is, the lower the temperature in the column is. As a result, production of ethylene glycol as a by-product from ethylene oxide in the column tends to be suppressed. However, ethylene oxide is relatively easily ignitable. Therefore, from a viewpoint of preventing leakage of oxygen into the system, usually, the operation is not performed at atmospheric pressure or lower, and is performed at a pressure a little higher than atmospheric pressure. As for temperature conditions of the stripper column 11, the column top temperature is preferably 101 to 115° C., and the column bottom temperature is preferably 101 to 110° C.

As illustrated in FIG. 2, the absorption liquid as a remaining part after ethylene oxide is stripped is extracted as the column bottom liquid of the stripper column 11, supplied to an upper part of the absorption column 2 as the absorption liquid of the absorption column 2, and can be circulated and used. In order to adjust the composition of the absorption liquid, fresh water or the above-described additive as necessary may be supplied to the absorption column 2 through a conduit disposed separately. The concentration of ethylene glycol in the absorption liquid supplied to the absorption column 2 is preferably maintained constant. Therefore, a part of the absorption liquid circulating between the absorption column 2 and the stripper column 11 is extracted from the column bottom part of the stripper column 11. Here, the column bottom liquid of the stripper column 11 does not contain ethylene oxide substantially. Specifically, the concentration of ethylene oxide contained in the column bottom liquid is preferably 10 ppm by weight or less, more preferably 0.5 ppm by weight or less. The column bottom liquid contains ethylene glycol produced in the absorption liquid as a by-product between the ethylene oxidation reaction step and the ethylene oxide stripping step. Apart thereof is extracted through a conduit 21 or 22. The extracted liquid is subjected to a combustion treatment or an ethylene glycol concentration step for concentrating and recovering ethylene glycol contained therein. Furthermore, in some cases, it is possible to recover ethylene glycol contained in the extracted liquid as a fiber grade product by performing a chemical treatment and, in some cases, a physical treatment to the ethylene glycol as it is or the ethylene glycol after being subjected to the ethylene glycol concentration step. The chemical treatment is, for example, disclosed in JP 45-9926 B or JP 04-28247 B.

The column bottom liquid of the stripper column 11 also contains a low boiling point impurity such as formaldehyde and a high boiling point impurity such as acetaldehyde or acetic acid. Therefore, as described above, accumulation of these impurities in the absorption liquid circulated into the absorption column 2 can be advantageously prevented by extracting a part thereof to the outside of the system.

The ethylene oxide-containing stripped substance stripped from the column top part of the stripper column 11 is fed through the conduit 20 to a stripper column condenser 25 in which cooling water passes through conduits 23 and 24. The condensed liquid is refluxed to the column top part of the stripper column 11 through a conduit 26. Uncondensed steam is supplied to a dehydrating column 28 (FIG. 3) through a conduit 27.

The ethylene oxide-containing steam supplied to the dehydrating column 28 comes into contact with a liquid to be refluxed through a conduit 29, and becomes steam having a higher concentration of ethylene oxide. A liquid extracted from the column bottom and having a low concentration of ethylene oxide is fed to the stripper column condenser 25 through a conduit.

The ethylene oxide-containing steam discharged from the column top part of the dehydrating column 28 is fed through a conduit 30 to a dehydrating column condenser 33 in which cooling water passes through conduits 31 and 32. A part of the condensed liquid is refluxed to the column top part of the dehydrating column 28 through the conduit 29. Uncondensed steam (ethylene oxide-containing uncondensed gas) of the dehydrating column condenser 33 is supplied to an ethylene oxide reabsorption column (hereinafter, also simply referred to as "reabsorption column") 35 illustrated in FIG. 1 through a conduit 34.

The remaining part of the condensed liquid of the dehydrating column condenser 33 is supplied to a light fraction separation column 37 through a conduit 36. Ethylene oxide steam containing a light fraction is heated using a heater 38 of the light fraction separation column 37 with a heating medium such as water vapor through a conduit 39, and is fed through a conduit 40 from the column top part of the light fraction separation column 37 to a light fraction separation column condenser 43 in which cooling water passes through conduits 41 and 42. The condensed liquid is refluxed to the column top part of the light fraction separation column 37 through a conduit 44. The uncondensed steam (ethylene oxide-containing uncondensed gas) of the light fraction separation column condenser 43 is supplied through a conduit 45 to the reabsorption column 35 illustrated in FIG. 1 to recover ethylene oxide.

The column bottom liquid of the light fraction separation column 37 is supplied to an ethylene oxide purification column (hereinafter, also simply referred to as "purification column") 47 through a conduit 46. Water vapor having a pressure of about 0.05 to 0.10 MPa gauge is supplied to a heater 48 of the purification column 47 to perform purification at a column bottom temperature of the purification column 47 of 35 to 80° C. at a column bottom pressure of the purification column 47 of 0.10 to 0.80 MPa gauge. Ethylene oxide steam having a column top temperature of 35 to 75° C. and a column top pressure of 0.10 to 0.80 MPa gauge is fed from the column top part of the purification column 47 to a purification column condenser 51 in which cooling water passes through conduits 49 and 50. Ethylene oxide is liquefied. Apart thereof is supplied to the column top part of the purification column 47 through a conduit 52 as a reflux liquid, and the remaining part is extracted through a conduit 53 as a product ethylene oxide (product EO). The uncondensed steam (ethylene oxide-containing uncondensed gas) of the purification column condenser 51 is supplied through a conduit 54 to the reabsorption column 35 illustrated in FIG. 1 to recover ethylene oxide.

The column bottom liquid of the purification column 47 is extracted through a conduit 55 if necessary to separate a heavy fraction of a high boiling point impurity such as acetaldehyde, water, or acetic acid.

As described above, the uncondensed steam discharged from the purification system (in the embodiment illustrated in FIG. 3, uncondensed steam derived from the dehydrating column condenser 33, the light fraction separation column condenser 43, and the purification column condenser 51) contains ethylene oxide. Therefore, the uncondensed steam is supplied to the reabsorption column 35 illustrated in FIG. 1.

In the reabsorption column 35, as in the absorption column 2, ethylene oxide is reabsorbed by counter flow contact with the absorption liquid. Here, the composition and the pH of the absorption liquid used for reabsorption of ethylene oxide in the reabsorption column 35, forms of the reabsorption column (plate column type or packed column type), and the like are similar to those described above for the absorption column 2. Therefore, detailed description thereof will be omitted here. Meanwhile, the present invention is characterized by operation pressure of the reabsorption column 35. In the related art, the operation pressure of the reabsorption column 35 is set to about 100 to 150 kPa gauge (refer to Comparative Example described later). On the other hand, in the present invention, as shown in Example described later, the operation pressure of the reabsorption column 35 is set to 3 to 50 kPa gauge. The present inventors have studied and found that, by such a constitution, surprisingly, an amount of ethylene glycol produced as a by-product is reduced and a yield of ethylene oxide is improved in a process for producing ethylene oxide. In addition, as a result thereof, it has been found that such an industrially extremely advantageous effect as follows is exhibited. That is, an amount of steam required for concentration of ethylene glycol as a by-product to be discharged to the outside of the system of the process for producing ethylene oxide, or an input amount of water necessary when the ethylene glycol as a by-product is discharged to the outside of the system, is reduced. A mechanism by which such an excellent effect is exhibited is estimated to be as follows. That is, by reduction in the operation pressure of the stripper column which is an upstream step of the reabsorption column, the operation temperature of the stripper column and the temperature of the absorption liquid passing through the conduits from the absorption column to the stripper column are lowered to suppress production of ethylene glycol as a by-product. Preferably, a pressure control valve is not disposed in the conduit 20, 27, or 34 leading to the ethylene oxide reabsorption column 35 from the ethylene oxide stripper column 11 through the dehydrating column 28.

The column bottom liquid of the reabsorption column 35 is circulated into the purification system (in the present embodiment, specifically the stripper column 11) through a conduit 56 similarly to the above-described column bottom liquid of the absorption column 2. In more detail, the column bottom liquid of the reabsorption column 35 is circulated into the conduit 12 illustrated in FIG. 2, heated in advance, and then introduced into the stripper column 11.

On the other hand, the uncondensed gas not absorbed in the reabsorption column 35 is discharged from the column top part of the reabsorption column 35 through a conduit 57. In one embodiment, the uncondensed gas discharged through the conduit 57 is boosted by a gas compressor 58, and then is circulated into the absorption column 2. However, the uncondensed gas discharged from the column top part of the reabsorption column 35 contains a large amount of carbon dioxide gas (usually about 5 to 60% by volume). Therefore, when the uncondensed gas is circulated into the absorption column 2, an amount of the carbon dioxide gas in the gas supplied from the absorption column 2 to the carbon dioxide gas absorption column 7 is increased. Then, an amount of the carbon dioxide gas treated in the carbon dioxide gas absorption column 7 and the carbon dioxide gas stripper column 8 is increased. It may be necessary to increase an amount of steam input into the reboiler 9 of the carbon dioxide gas stripper column 8 or to increase an input amount of a carbon dioxide gas absorption promoter. Therefore, the uncondensed gas discharged from the column top part of the reabsorption column 35 through the conduit 57 may be supplied to the carbon dioxide gas absorption column 7 after being boosted by the gas compressor 58. By such a constitution, a flow rate of the gas supplied to the carbon dioxide gas absorption column 7 increases only a little. However, as described above, the uncondensed gas discharged from the column top part of the ethylene oxide reabsorption column contains a large amount of carbon dioxide gas (usually about 5 to 60% by volume). Therefore, when the ethylene oxide-containing uncondensed gas discharged from the column top part of the reabsorption column 35 is supplied to the carbon dioxide gas absorption column 7, the concentration of the carbon dioxide gas in the gas supplied to the carbon dioxide gas absorption column 7 increases a little. In this way, according to the present invention, by introducing a gas containing a carbon dioxide gas with a higher concentration into a carbon dioxide gas system, various industrially advantageous effects can be exhibited.

A suction pressure of the gas compressor 58 for boosting the uncondensed gas discharged from the column top part of the reabsorption column 35 through the conduit 57 is preferably low. Specifically, the suction pressure is preferably 3 to 5 kPa gauge. By such a constitution, it is possible to prevent oxygen from entering the gas compressor 58 from the atmosphere.

The uncondensed gas discharged from the column top part of the reabsorption column 35 contains ethylene as a reaction raw material. However, as described above, the unabsorbed gas discharged from the column top part of the carbon dioxide gas absorption column 7 is circulated into the ethylene oxidation reactor 1 through the conduit 3. Ethylene is hardly absorbed in the carbon dioxide gas absorption column 7. Therefore, even if the above-described constitution is employed, there is no possibility that ethylene as a reaction raw material is lost.

Examples

Hereinafter, the embodiment of the present invention will be described in more detail using Example. However, the technical range of the present invention is not limited only to the following embodiment.

Comparative Example

Figure 3:
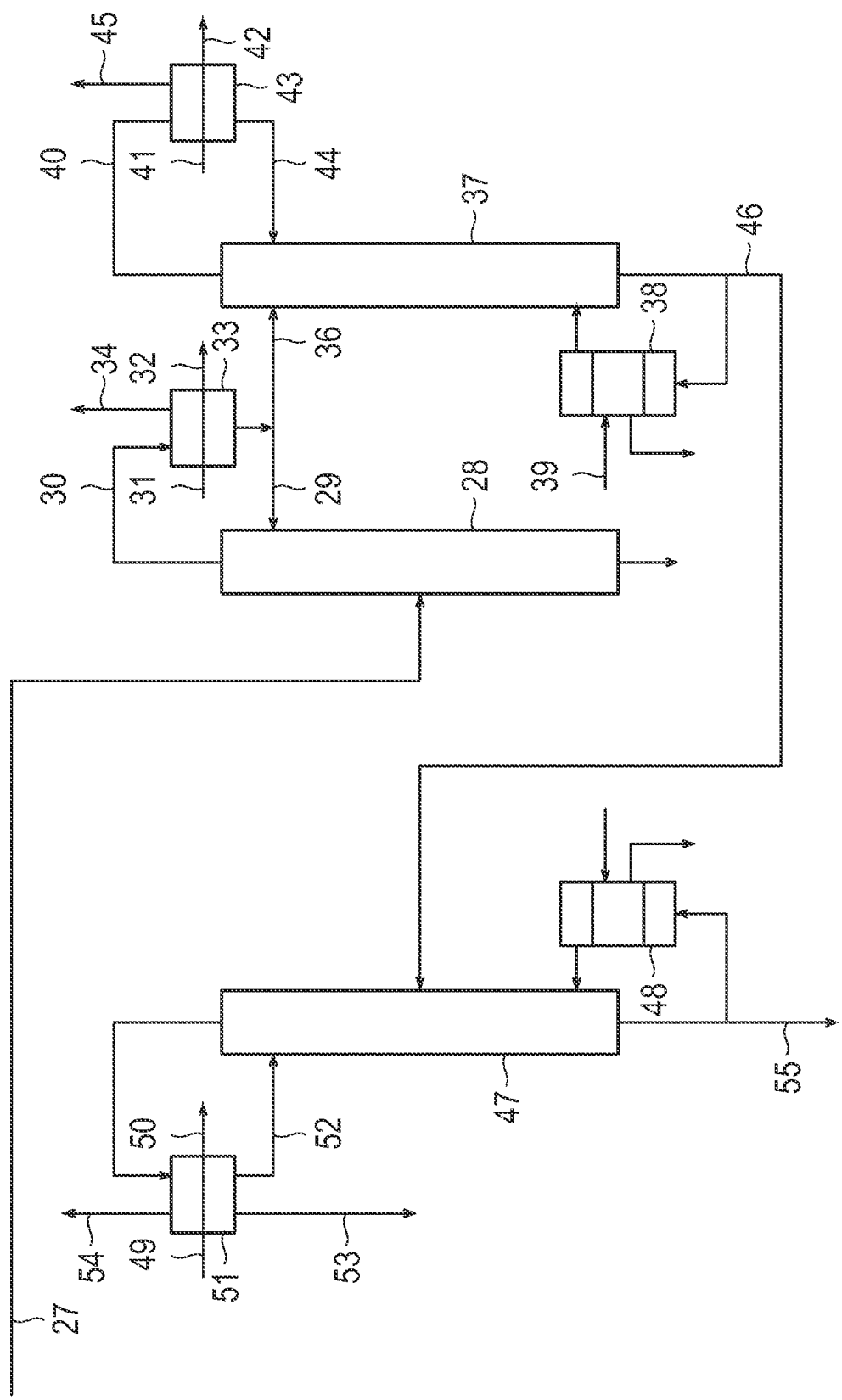
FIG. 3 is a block diagram illustrating a constructive example of a purification step until the stripped ethylene oxide is finally purified.

Ethylene oxide was produced by a process for producing ethylene oxide illustrated in FIGS. 1 to 3. At this time, the operation pressure (column top pressure) of the reabsorption column 35 was set to 120 kPa gauge.

Example

Ethylene oxide was produced by a process for producing ethylene oxide illustrated in FIGS. 1 to 3. At this time, the operation pressure (column top pressure) of the reabsorption column 35 was set to 10 kPa gauge.

As a result of performing the above-described production processes according to Comparative Example and Example, various operation conditions of the ethylene oxide stripper column are shown in Table 1.

TABLE 1

| Operation conditions | Example | Comparative Example |
| --- | --- | --- |
| Operation pressure of reabsorption column (column top) [kPa gauge] | 10 | 120 |
| Column top pressure of stripper column [kPa gauge] | 30 | 140 |
| Column bottom pressure of stripper column [kPa gauge] | 38 | 148 |
| Column bottom temperature of stripper column [° C.] | 110 | 128 |

As a result of performing the above-described production processes according to Comparative Example and Example, flow rates of ethylene oxide in the respective portions in the production processes are shown in Table 2.

TABLE 2

| Operation conditions | Example | Comparative Example |
| --- | --- | --- |
| Flow rate of ethylene oxide supplied to absorption column [kg/hr] | 100 | 100 |
| Flow rate of ethylene oxide at column top of absorption column [kg/hr] | 0 | 0 |
| Flow rate of ethylene oxide at column top of stripper column [kg/hr] | 97 | 92 |
| Flow rate of ethylene oxide at column bottom of stripper column [kg/hr] | 0 | 0 |
| Yield of ethylene oxide [%] | 97 | 92 |

As clear from the result shown in Table 2, in the present Example, the yield of ethylene oxide is largely increased compared to that in Comparative Example. In addition, as a secondary effect brought by the improved yield of ethylene oxide, such an effect as follows is exhibited. That is, an amount of steam required for concentration of ethylene glycol as a by-product to be discharged to the outside of the system of the process for producing ethylene oxide, or an input amount of water necessary when the ethylene glycol as a by-product is discharged to the outside of the system, is reduced.

From the above-described comparison between Example and Comparative Example, it has been indicated that the method for producing ethylene oxide in the process for producing ethylene oxide according to the present invention brings various advantageous effects in the process for producing ethylene oxide. In view of a production amount of ethylene oxide of hundreds of thousands tons per year, industrial contribution of the present invention is immeasurable.

The present application is based on the Japanese patent application No. 2013-074174 filed on Mar. 29, 2013. The disclosed contents thereof are referred to and incorporated here as a whole.

REFERENCE SIGNS LIST

1: ethylene oxidation reactor
2: ethylene oxide absorption column
4: boosting blower
7: carbon dioxide gas absorption column
8: carbon dioxide gas stripper column
9: reboiler
10: gas-liquid contact part
11: ethylene oxide stripper column
13: heat exchanger
14: heater
16: gas-liquid separation tank
19: stripper column heater
25: stripper column condenser
28: dehydrating column
33: dehydrating column condenser
35: ethylene oxide reabsorption column
37: light fraction separation column
38: light fraction separation column heater
43: light fraction separation column condenser
47: ethylene oxide purification column
48: purification column heater
51: purification column condenser
58: gas compressor

The invention claimed is:

1. A method for producing ethylene oxide comprising:
supplying an ethylene oxide-containing reaction product gas produced in an ethylene oxidation reaction step, in which ethylene is subjected to catalytic gas phase oxidation using a molecular oxygen-containing gas in the presence of a silver catalyst, to an ethylene oxide absorption column;
bringing the reaction product gas into contact with an absorption liquid supplied to the ethylene oxide absorption column;
supplying an ethylene oxide-containing column bottom liquid of the ethylene oxide absorption column to an ethylene oxide purification system;
supplying an ethylene oxide-containing uncondensed gas discharged from the ethylene oxide purification system to an ethylene oxide reabsorption column and
circulating the column bottom liquid of the ethylene oxide reabsorption column to the ethylene oxide stripper column, and wherein
an operation pressure (column top pressure) of the ethylene oxide reabsorption column is set to 3 to 50 kPa gauge.

2. The production method according to claim 1, wherein the operation pressure (column top pressure) of a ethylene oxide stripper column is set to 3 to 60 kPa gauge.

3. The production method according to claim 1, wherein the method further comprises supplying an uncondensed as to the ethylene oxide reabsorption column from the ethylene oxide stripper column through an ethylene oxide dehydrating column, and wherein
a pressure control valve is not disposed in a conduit for supplying an uncondensed gas.

4. The production method according to claim 1, wherein a suction pressure of a compressor used for boosting the uncondensed gas of the ethylene oxide reabsorption column is 3 to 5 kPa gauge.

5. The method for producing ethylene oxide according to claim 1, comprising:
supplying the ethylene oxide-containing uncondensed gas discharged from a column top part of the ethylene oxide reabsorption column to a carbon dioxide gas absorption column; and
recovering a carbon dioxide gas.

* * * * *